United States Patent [19]

Kesling

[11] Patent Number: 4,551,094
[45] Date of Patent: Nov. 5, 1985

[54] EDGEWISE BRACKET WIRE RETAINING CLIP

[76] Inventor: Peter C. Kesling, 611 W. 250 S., LaPorte, Ind. 46350

[21] Appl. No.: 696,783

[22] Filed: Jan. 31, 1985

[51] Int. Cl.[4] .................................................. A61C 7/00
[52] U.S. Cl. ............................................. 433/8; 433/17
[58] Field of Search ..................... 433/8, 9, 13, 6, 17

[56] References Cited

U.S. PATENT DOCUMENTS

| | | |
|---|---|---|
| 1,890,487 | 12/1932 | Angle . |
| 2,767,469 | 10/1956 | Gladstone ............................ 433/13 |
| 3,128,552 | 4/1964 | Broussard . |
| 3,391,461 | 7/1968 | Johnson . |
| 3,497,954 | 3/1970 | Kesling . |
| 3,838,514 | 10/1974 | Polak ...................................... 433/17 |
| 4,023,274 | 5/1977 | Wallshein . |
| 4,355,975 | 10/1982 | Fujita . |
| 4,492,573 | 1/1985 | Hanson . |

OTHER PUBLICATIONS

"American Journal of Orthodontics", vol. 86, No. 1, Jul. 1984, pp. 1A–3A.

*Primary Examiner*—Robert Peshock
*Attorney, Agent, or Firm*—Lloyd L. Zickert

[57] ABSTRACT

An orthodontic clip or cap removably snap mountable on an edgewise bracket for retaining an archwire in the archwire slot of the bracket and having means for enhancing rotational tipping and/or torque control.

14 Claims, 10 Drawing Figures

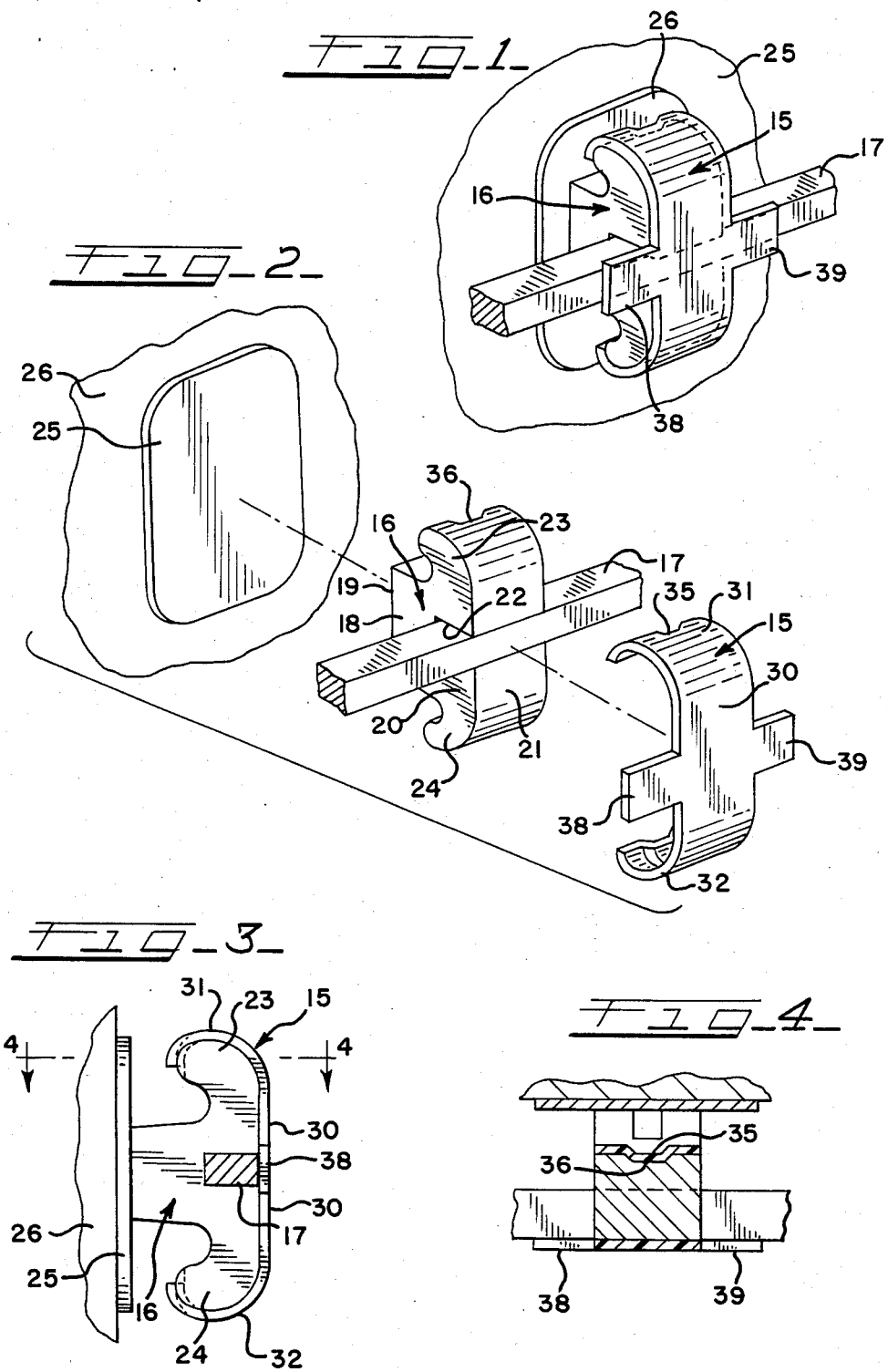

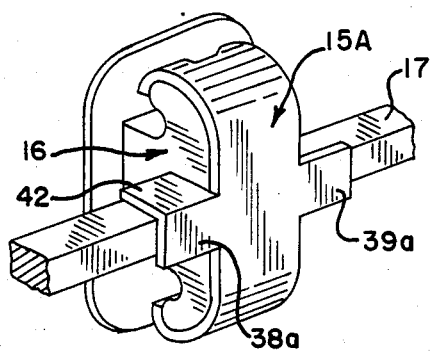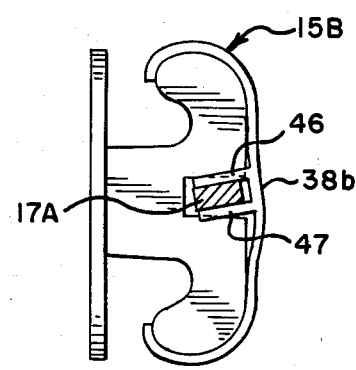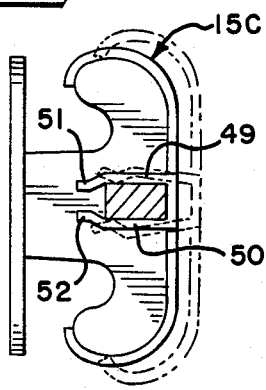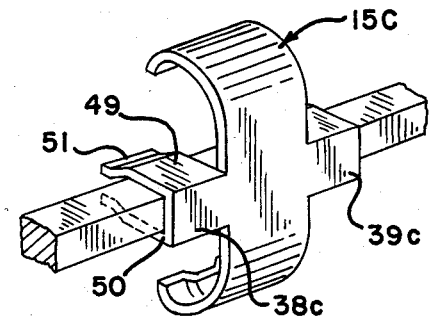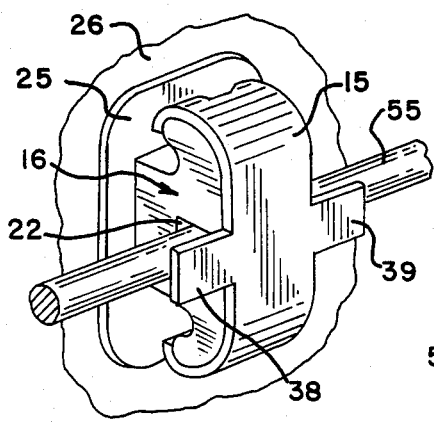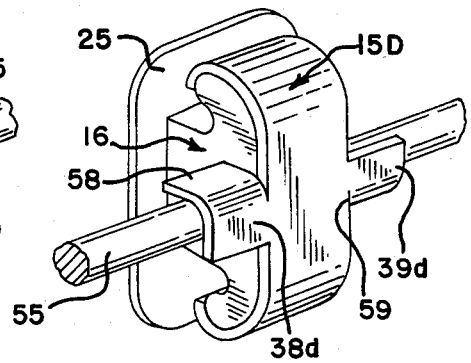

EDGEWISE BRACKET WIRE RETAINING CLIP

DESCRIPTION

This invention relates in general to an orthodontic appliance, and more particularly to a removable cap or clip adaptable to be used with an edgewise bracket for retaining an archwire in the archwire slot of the bracket, and still more particularly to a removable cap for enhancing rotational control with respect to the tooth on which the bracket is mounted.

BACKGROUND OF THE INVENTION

With the advent of the trend to construct brackets in smaller sizes and particularly to construct edgewise brackets with narrower mesiodistal dimensions, the control of forces between the archwire and the bracket has diminished for the obvious reason that there is less contact between the archwire and the bracket. It therefore becomes evident that there is a need to enhance force control between the archwire and these newly developed brackets in order to obtain suitable orthodontic treatment. One manufacturer has attempted to solve this problem by adding extensions to the mesial and distal sides of the bracket at the archwire slot so as to provide mesial and distal support for the lingual side of the archwire. There are no other known structures directed toward solving this problem.

Heretofore, it has been known to provide archwire retention clips or caps for edgewise brackets, such as shown in U.S. Pat. Nos. 3,128,552 and 4,023,274. However, these clips, along with other known clips, do not include extensions in the mesial and distal sides of the caps for enhancing rotational control.

SUMMARY OF THE INVENTION

It is therefore an object of the present invention to provide an improved edgewise bracket wire retaining clip capable of enhancing rotational control.

It is a further object of the present invention to provide a new and improved archwire retaining clip or cap that is especially useful on the newly designed narrower edgewise brackets that includes extensions at the mesial and distal sides of the cap for providing any or all of additional rotational, tipping and torque control.

Other objects, features and advantages of the invention will be apparent from the following detailed disclosure, taken in conjunction with the accompanying sheets of drawings, wherein like reference numerals refer to like parts, in which:

BRIEF DESCRIPTION OF THE DRAWINGS

FIG. 1 is a perspective view of an edgewise bracket mounted on a pad which is in turn mounted on a tooth surface and showing a rectangular wire in the archwire slot of the bracket and the removable cap or clip of the invention in place on the bracket for retaining the archwire in the archwire slot and for enhancing rotational control;

FIG. 2 is a generally exploded perspective view of the assembly shown in FIG. 1;

FIG. 3 is a side elevational view of the assembly shown in FIG. 1 and illustrating the archwire in cross section;

FIG. 4 is a detailed cross-sectional view taken substantially along line 4—4 of FIG. 3, illustrating the detent-indent arrangement for preventing lateral movement of the cap on the bracket;

FIG. 5 is a view similar to FIG. 1 but illustrating a modified archwire retaining cap providing additional tipping and torque control;

FIG. 6 is a side elevational view of an assembly showing a still further modified cap applicable for providing rotation, tip and torque control where the archwire is sized substantially smaller than the archwire slot of the bracket;

FIG. 7 is a side elevational view of an assembly with a still further modified cap which incorporates clips with the extensions for the purpose of permitting the cap to be self-retaining with respect to the archwire prior to being mounted on the bracket;

FIG. 8 is a perspective view of the cap of FIG. 7 mounted on an archwire with the clips prior to mounting the archwire and cap on the bracket;

FIG. 9 is a perspective view like FIG. 1 but illustrating the retention of a round wire rather than a rectangular wire; and FIG. 10 is a perspective view of an assembly illustrating a still further modified removable cap or clip for retaining a round archwire on the bracket slot.

DESCRIPTION OF THE INVENTION

Referring now to the drawings, and particularly to FIGS. 1 to 4, a removable cap or clip according to the invention and generally designated by the numeral 15 is illustrated in mounted arrangement on an edgewise bracket 16 for retaining an archwire 17 on the bracket. The bracket 16 includes a base portion 18 having a lingual attaching surface 19 and an archwire receiving portion 20 having a buccal surface 21 in which there is disposed a rectangular horizontally opening archwire slot 22. The wire receiving portion further includes upper and lower tie wings 23 and 24 on opposite sides of the archwire slot at opposite sides of the archwire slot 22.

The lingual surface 19 of the bracket 16 is suitably attached to a bracket pad 25 that is in turn suitably bonded to a tooth 26. It can be appreciated that the bracket may alternately be attached to a tooth band which is then cemented to the tooth.

The bracket 16 would generally be made of a suitable stainless steel by machining or casting, although it could be made of plastic. When made of metal, it will be appreciated that the bracket pad will likewise be made of a suitable metal and the bracket may be suitably attached to the pad or to a band by welding or soldering. It may be further appreciated that the archwire slot will be sized for use with a given size of wire and positioned or angulated to produce whatever force is desired for a particular tooth. For simplicity purposes, it is illustrated as being of a standard type without any built-in torque or angulation.

The removable cap 15 of the invention includes generally a front panel 30 adapted to have a mesiodistal width substantial to that of the bracket and to overlie the buccal surface 21 of the bracket. Upper and lower retention hooks 31 and 32 are integrally formed with the front panel and for mating relation with the upper and lower tie wings of the bracket on which it is to be mounted. As illustrated particularly in FIG. 3, the retention hooks fit over the tie wings 23 and 24. It will be appreciated that the removable cap is made of a springy material so that it will deform when applied buccally to the bracket and snap into place when it is fitted on the bracket, as illustrated in FIG. 3. Generally the cap will be made of a suitable spring steel that will be compatible with the material from which the bracket and archwire are made. The archwire could likewise be made of a suitable spring steel. However, it can be appreciated that the cap could be made of a suitable plastic, especially if it is used on a plastic bracket, although it could be made of plastic even if used on a metal bracket.

In order to prevent lateral or mesiodistal movement of the cap relative to the bracket, a detent-indent arrangement is provided wherein each of the retention hooks 31 and 32 includes detents 35 that coact with indents 36 formed in the tie wings. It is therefore apparent that upon mounting of the cap onto the bracket, it will self-center on the bracket when the detents on the cap coact with the indents on the bracket, and they will then thereafter inhibit lateral movement relative to the cap.

The cap further includes mesial and distal extensions 38 and 39 which respectively extend from the mesial and distal edges of the cap in the area where the cap aligns with the archwire so that the extensions are in overlying engagement with the archwire mesial and distal to the bracket, thereby enhancing the rotational control between the archwire and the bracket and compensating for the narrower width of the bracket so as to provide more efficient orthodontic treatment. The total overall length of the extensions are greater than the bracket width and such as to give the desired rotational control, and the extension width along the vertical of the cap is preferably slightly greater than the width of the archwire slot and archwire as illustrated in the drawings. However, it could be appreciated that the width could be equal to the width of the archwire. It may therefore be seen that the cap not only serves to retain the archwire in place on the bracket but also to enhance the rotational control between the archwire and the bracket.

A modified removable cap 15A is illustrated in FIG. 5 retaining the archwire 17 on the bracket 16 and which differs from the removable cap 15 in that one or more tabs or wings are provided on at least one of the extensions for the purpose of applying tip and/or torque control. The like parts of this cap and other modifications are designated with the same legends and a corresponding suffix letter a, whereby the extensions are designated 38a and 39a. A tab or wing 42 projects lingually from the upper edge of the extension 38a to overlie the upper surface of the archwire 17 and thereby provide tip control between the archwire and the bracket. While not shown, similar tabs or wings may extend from the other rotation extension 39a and along either the occlusal or gingival surface of the archwire 17.

A further modified removable cap 15B is shown in FIG. 6 which differs from the embodiment shown in FIG. 1 in that the extension 38b includes lingually projecting upper and lower tabs or wings 46 and 47 to closely engage an archwire 17A which is of a smaller cross-sectional dimension than the cross-sectional dimension of the archwire slot, whereby it may assume various positions relative to the slot in a situation where a torquing force is being applied between the wire and the bracket. Inasmuch as the cap is springy or flexible and is shown in position to be slightly flexed in its front panel, the cap could serve to soften the torquing action where that would be desired. The lingually projecting tabs or wings could be provided on one or both of the cap extensions depending upon need.

A still further modified removable cap 15C is shown in FIGS. 7 and 8 which differs from the embodiment of FIG. 1 in that at least one of the extensions are additionally in the form of a clip that enables the cap to first be clipped to the wire and then thereafter simultaneously mounted with the wire onto the bracket. Alternately, the wire could be first mounted in the bracket and the cap with clips then mounted simultaneously on the bracket and the wire as illustrated in phantom on FIG. 7. The clips may be provided on one or both of the extensions, but extensions 38c and 39c of cap 15C are shown as being provided with clips wherein upper and lower wings or tabs 49 and 50 project lingually from the extension and terminate beyond the wire with end tabs 51 and 52 extending toward each other. Thus, the tabs 49, 50, 51 and 52 coact with the extensions 38c and 39c to form clips. Where clips are formed on each side of the cap body, which when in position on a bracket are disposed at opposite sides of the bracket, it is not necessary to provide the detent-indent arrangement shown in the embodiment of FIGS. 1 to 4 to prevent lateral movement between the cap and bracket, as the clips prevent lateral movement. Additionally, it may be appreciated that the tabs 49 and 50, together with the tabs 51 and 52, enhance the tipping and torquing control between the wire and the bracket.

The use of a round wire in the edgewise bracket and being retained in place by the removable cap of the invention is illustrated in FIG. 9 wherein a round wire 55 is disposed in the archwire slot 22 and retained in place on the bracket 16 by the removable cap 15. In this assembly, the extensions 38 and 39 enhance rotational control between the archwire and the bracket, and such an assembly would be used where there is a desire not to have any torquing control between the wire and the bracket.

The assembly in FIG. 10 illustrates a further modified removable cap 15D for use with the edgewise bracket 16 where the round wire 55 is disposed in the archwire slot and where it is desired to additionally have tipping control. Accordingly, the removable cap 15D includes tip tabs or wings 58 and 59 projecting lingually from the rotational extensions 38d and 39d. The tip wing 58 overlies one side of the wire, while the tip wing 59 overlies the opposite side. The tabs or wings are preferably disposed on opposite sides of the cap such that they fit closely with opposite sides of the bracket, and then they produce the function of preventing lateral movement and eliminate the need for the detent-indent arrangement in FIGS. 1 to 4.

It is therefore appreciated that the removable cap or clips of the present invention is particularly useful for enhancing rotational control on edgewise brackets of narrow width and is also capable of additionally enhancing tip and torque control where needed.

It will be understood that modifications and variations may be effected without departing from the scope of the novel concepts of the present invention, but it is understood that this application is to be limited only by the scope of the appended claims.

I claim:

1. In combination with an orthodontic bracket having a base adapted to be secured to a bracket pad or a tooth band and a body extending buccally from the base, said body having a buccal surface, a horizontally opening archwire slot along the buccal surface to receive an archwire, and a pair of tie wings on opposite sides of said slot, the improvement in a removable cap receivable on said body to retain the archwire in the slot and to enhance rotational control, said cap having a body of substantially the same width as that of the bracket, upper and lower retention hooks for engaging over the tie wings, and mesial and distal extensions generally coplanar with the body for engaging the buccal surface of the archwire to enhance rotational control.

2. The removable cap defined in claim 1, wherein the retention hooks include means coacting with the tie wings to inhibit mesiodistal movement of the cap.

3. The removable cap defined in claim 1, wherein at least one of said extensions includes a lingually projecting tab adapted to engage along one of the occlusal or gingival sides of the archwire to limit mesial or distal tipping.

4. The removable cap defined in claim 1, wherein each of said extensions includes a lingually projecting tab adapted to engage one of the occlusal or gingival sides of the archwire to limit mesiodistal tipping.

5. The removable cap defined in claim 1, where in at least on of said extensions includes upper and lower lingually projecting tabs adapted to engage along the occlusal and gingival sides of the archwire to limit mesiodistal tipping.

6. The removable cap defined in claim 5, wherein the tabs have terminal end portions bent toward each other to define retaining clips that inhibit buccal movement of the cap from the archwire.

7. The removable cap defined in claim 1, wherein the archwire cross section is smaller than that of the bracket slot, and at least one of said extensions includes upper and lower lingually projecting tabs adapted to engage closely along the occlusal and gingival sides of the archwire to limit mesiodistal tipping and to apply a torque.

8. The removable cap defined in claim 1, wherein each of said extensions includes a lingually projecting tab, one of said tabs adapted to engage the occlusal side of the archwire and the other of said tabs adapted to engage the gingival side of the archwire.

9. The removable cap defined in claim 2, wherein at least one of said extensions includes a lingually projecting tab adapted to engage along one of the occlusal or gingival sides of the archwire to limit mesial or distal tipping.

10. An orthodontic spring clip for use with an orthodontic bracket and an archwire received by the bracket, said bracket including a base portion having a lingual surface adapted to be secured to a bracket pad or band, and a wire receiving portion at the buccal side of the base portion having a buccal surface with a generally horizontal archwire slot and a pair of tie wings on opposite sides of the slot, said clip being snappable onto the buccal surface of the wire receiving portion over the tie wings to retain an archwire in the bracket slot and comprising a front panel of substantially the same width as the bracket overlying the buccal surface of the bracket, upper and lower retention hooks fitting over the tie wings, means coacting with the bracket to prevent lateral movement of said clip, and extensions at the mesial and distal edges of said front panel in overlying relation with the archwire to enhance rotational control.

11. The combination defined in claim 10, wherein said means includes detents on the retention hooks mating with indents on said tie wings.

12. The combination defined in claim 10, wherein said clip further comprises means on said extensions for producing tipping and/or torque control.

13. The combination defined in claim 10, wherein said at least one of said extensions includes means for retaining the clip onto the archwire prior to inserting the archwire into the slot and snapping the clip onto the bracket.

14. The combination defined in claim 10, wherein both extensions include means for retaining the clip onto the archwire prior to inserting the archwire into the slot and snapping the clip onto the bracket, said retaining means further closely fitting on opposite sides of the bracket to serve as said means for coacting with the bracket to prevent lateral movement of the clip.

* * * * *

UNITED STATES PATENT AND TRADEMARK OFFICE
CERTIFICATE OF CORRECTION

PATENT NO. : 4,551,094
DATED : November 5, 1985
INVENTOR(S) : PETER C. KESLING

It is certified that error appears in the above-identified patent and that said Letters Patent are hereby corrected as shown below:

Col. 2, line 12, after "modified" insert --removable--;

Col. 5, line 25, change "on" to --one--.

Signed and Sealed this

Fourth Day of February 1986

[SEAL]

Attest:

DONALD J. QUIGG

Attesting Officer     Commissioner of Patents and Trademarks